(12) United States Patent
Naubereit

(10) Patent No.: US 12,044,842 B2
(45) Date of Patent: Jul. 23, 2024

(54) BEAM DEFLECTION DEVICE FOR A LASER DEVICE, LASER DEVICE AND METHOD FOR GENERATING A LASER PATTERN

(71) Applicant: SCHWIND eye-tech-solutions GmbH, Kleinostheim (DE)

(72) Inventor: Pascal Naubereit, Aschaffenburg (DE)

(73) Assignee: SCHWIND eye-tech-solutions GmbH, Kleinostheim (DE)

( * ) Notice: Subject to any disclaimer, the term of this patent is extended or adjusted under 35 U.S.C. 154(b) by 400 days.

(21) Appl. No.: 17/321,017

(22) Filed: May 14, 2021

(65) Prior Publication Data
US 2021/0364783 A1 Nov. 25, 2021

(30) Foreign Application Priority Data

May 20, 2020 (DE) ...................... 10 2020 113 693.5

(51) Int. Cl.
*G02B 26/10* (2006.01)
*A61F 9/008* (2006.01)
*G02B 26/08* (2006.01)

(52) U.S. Cl.
CPC ............ *G02B 26/101* (2013.01); *A61F 9/008* (2013.01); *G02B 26/0833* (2013.01); *G02B 26/0883* (2013.01); *A61F 2009/00897* (2013.01)

(58) Field of Classification Search
CPC .............. G02B 26/101; G02B 26/0833; G02B 26/0883; G02B 26/085; G02B 26/0816; A61F 9/008; A61F 2009/00897; A61F 9/00802; A61F 9/00825; A61F 2009/00872
See application file for complete search history.

(56) References Cited

U.S. PATENT DOCUMENTS

| 7,842,901 B2 | 11/2010 | Wawers et al. |
| 9,931,712 B2 | 4/2018 | Wang |
| 2014/0114295 A1 | 4/2014 | Stobrawa et al. |
| 2019/0015251 A1 | 1/2019 | Rathjen |

FOREIGN PATENT DOCUMENTS

| DE | 10 2005 047 328 B3 | 12/2006 |
| DE | 10 2014 012 453 A1 | 2/2016 |
| EP | 2345394 A1 | 7/2011 |

OTHER PUBLICATIONS

Notification of the Second Office Action issued Apr. 19, 2024 in CN Appl. No. 202110545933.9.

*Primary Examiner* — Scott M. Getzow
(74) *Attorney, Agent, or Firm* — MEDLER FERRO WOODHOUSE & MILLS PLLC

(57) ABSTRACT

A beam deflection device for a laser device is disclosed for generating a laser pattern on or in a material by means of a laser beam) of the laser device. The beam deflection device includes at least one reflecting or dispersive beam offset element, which is formed for spatially offsetting the laser beam in relation to an optical axis of a laser generating device of the laser device. The beam deflection device further includes a rotating, dispersive optical element, which is formed for generating a rotation pattern as the laser pattern from the previously offset laser beam. Further, a laser device, a computer program as well as to a computer-readable medium are disclosed.

17 Claims, 1 Drawing Sheet

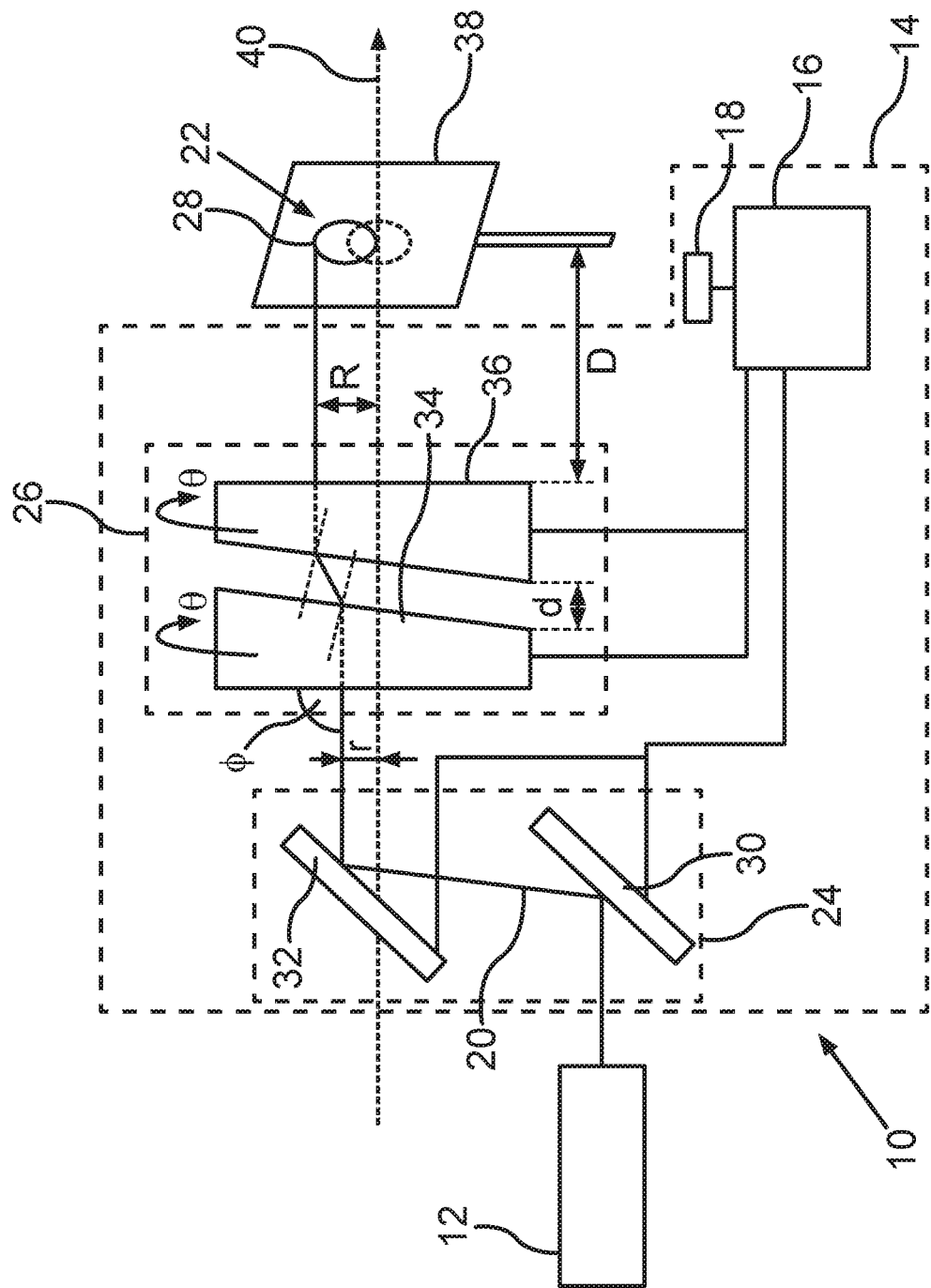

BEAM DEFLECTION DEVICE FOR A LASER DEVICE, LASER DEVICE AND METHOD FOR GENERATING A LASER PATTERN

The invention relates to a beam deflection device for a laser device for generating a laser pattern in or on a material by means of a laser beam of the laser device. Further, the invention relates to a laser device with at least one beam deflection device, to a method, to a computer program as well as to a computer-readable medium.

Beam deflection devices for laser devices are in particular known from the ophthalmology or for example in laser cutting. For example, the laser devices are employed in the ophthalmology for treating opacities and scars within a cornea, which can arise by inflammations, injuries or native diseases and thereby can impair the sight. In particular in case that these pathological and/or unnaturally altered areas of the cornea are located in the axis of vision of the eye, clear sight is considerably disturbed. Eye surgical laser devices are additionally used for the correction of visual disorders based on optical defects of the eye. In particular in the photorefractive keratectomy (PRK), in the laser-epithelial keratomileusis (LASIK), the epithelial laser in-situ keratectomy (Epi-LASIK) or the transepithelial photorefractive keratectomy (Trans-PRK), eye surgical lasers are employed. Hereto, different laser methods by means of corresponding treatment devices are given from the prior art, which can for example separate a volume body from the cornea and thus can improve the sight for a patient. These laser methods are an invasive procedure such that it is of particular advantage for the patient if the procedure is performed in a time as short as possible and to a particularly efficient extent.

It is the object of the present invention to provide a beam deflection device, a laser device, a method, a computer program as well as a computer-readable medium, by means of which a more efficient generation of a preset laser pattern in or on a material can be realized.

This object is solved by a beam deflection device, a laser device, a method for operating a laser device, a computer program as well as a computer-readable medium according to the independent claims. Advantageous forms of configuration with convenient developments of the invention are specified in the respective dependent claims, wherein advantageous configurations of the beam deflection device are to be regarded as advantageous forms of configuration of the laser device, of the method, of the computer program and of the computer-readable medium and vice versa.

A first aspect of the invention relates to a beam deflection device for a laser device for generating a laser pattern in or on a material by means of a laser beam of the laser device, with at least one reflecting or dispersive beam offset element, which is formed for spatially offsetting the laser beam in relation to an optical axis of a laser generating device of the laser device, and with a rotating, dispersive optical element, which is formed for generating a rotation pattern as the laser pattern from the previously offset laser beam.

Thus, a combination of the beam offsetting element and a rotating element of the beam deflection device is proposed, wherein the rotating optical element in particular enlarges and transfers the previously achieved beam offset into a rotation pattern, respectively. Thereby, the advantages of the different concepts, in other words of the beam offset and the rotation, can be combined with each other, whereby a more efficient generation of the laser pattern can be realized. Further, the corresponding disadvantages of the individual elements can be compensated for. For example, high times can be taken up with reflecting mirrors as the beam offset element to generate a rotationally symmetrical pattern. By the solution according to the invention, this can be prevented since the generation of the rotation pattern is not performed by the beam offset element, but by the rotating, dispersive optical element. Further, only small rotation patterns could be generated based on small mirrors as the beam offset element, which is compensated for by the solution according to the invention by the rotating, dispersive optical element. The dispersive optical element is at least one rotating element, which can generate vibrations in the rotation and in particular in the rotation for beam offset, whereby corresponding imaging errors can arise. By the combination of the reflecting or dispersive beam offset element with the rotating, dispersive optical element, these disadvantages are in turn cancelled since the beam offset is performed by the beam offset element. Thus, a synergistic effect of the beam offset element with the optical element is generated.

Thus, an efficient beam deflection device can be used for a laser device, which reduces the time for generating a corresponding rotation pattern and prevents corresponding imaging errors and vibrations at the same time. Presently, the laser pattern can also be referred to as scan pattern.

Presently, a cornea of a human or animal eye can for example be regarded as material, wherein a treatment of the cornea can then be performed by means of the laser device. If the beam deflection device should be employed for laser cutting, thus, the material to be cut, for example a metal, can be regarded as the material. Herein, the enumeration of the possibilities of employment of the beam deflection device is to be regarded as purely exemplary and not exhaustive at all. Thus, the beam deflection device can be employed in a plurality of laser devices.

According to an advantageous form of configuration, the beam offset element formed as reflecting comprises at least one micro-optical electromechanical mirror element. The micro-optical electromechanical mirror element is in particular also referred to as micro-electromechanical system (MEMS) mirror element. These MEMS mirrors are small components, which in particular combine logic elements and micromechanical structures, for example mirrors, in one component. In particular, it can be provided that the reflecting beam offset element comprises at least two micro-optical electromechanical mirror elements. Thus, it is in particular a MEMS mirror pair, which is also referred to as dual MEMS. They are preferably constructed biaxially to each other. By means of the dual MEMS, a parallel beam offset to the optical axis can be provided without angle alteration. By means of the dual MEMS, for example spiral patterns or other non-circular laser patterns can then be realized by means of synchronous position pre-compensation, wherein a decentered treatment on the eye is then for example possible. It can be understood by position pre-compensation that for a desired scan pattern, which is imaged by the rotating dispersive element, the rotation previously has to be compensated for by an appropriate movement of the beam offsetting element. For example, this can be realized by a predetermined point of impingement of the offset laser beam of the dual MEMS on the rotating, dispersive optical element.

Further, it has proven advantageous if the reflecting beam offset element comprises at least one galvanometer mirror or the dispersive beam offset element comprises at least one prism or at least one Risley prism or at least one Dove prism. In particular, the galvanometer mirror can be a so-called galvanometer scanner element. This element in particular has electromagnetically driven rotational axes, at the end of which mirrors for deflecting the laser beam are respectively located. By the use of a prism, a dispersion, in other words scattering, of the laser beam can in particular be generated. Thus, the beam offset can be performed based on the scattering. The Risley prism is in particular a special form of a prism, by means of which a beam offset is allowed with a simple form of configuration of the Risley prism. In particular, the Risley prism is formed as a cuboidal structure, wherein ten sides or five side surfaces are formed orthogonal to each other. Thus, a beam offset can be performed. The Dove prism is an optical prism, which is classed among the inverting reflective prisms. The light is refracted both on the entry and on the exit surface. Thus, it is allowed to offset the laser beam with different reflecting beam offset elements or with dispersive beam offset elements. Thereby, a substantially parallel beam offset in relation to the optical axis can in particular be generated.

Further, it has proven advantageous if the rotating, dispersive optical element is formed as a Risley prism pair. In particular, two Risley prisms are utilized in the Risley prism pair. They are used for enlarging and for transferring the scan pattern of the offset laser beam, respectively. In particular, the rotation of the laser pattern can be generated utilizing the Risley prism pair.

In a first alternative, respective Risley prisms of the Risley prism pair are arranged rigidly fixed to each other. Herein, the Risley prisms of the Risley prism pair can in particular be fixed at a relative angle of substantially 180 degrees to each other. By the relative angle of the two Risley prisms of 180 degrees, the influence of the Risley prisms on the respective beam profile becomes negligible, wherein vibrations are also negligible since a concentric construction and a rigid fixation of the aligned prisms to each other form a simplified system. Further, different rotational frequencies are not required for the different prisms such that a simple construction of the beam deflection device can be realized.

Further, the respective Risley prisms of the Risley prism pair can have a fixed distance to each other along the optical axis. Thereby, simple rotation patterns can be generated, wherein a simple control by means of a control device of the beam deflection device can be realized. Further, the mechanical construction of the beam deflection device is very simple such that an inexpensive and fail-safe beam deflection device is provided.

In a further alternative, the respective Risley prisms of the Risley prism pair can have a variable adjustable distance to each other along the optical axis. In other words, the distance between the respective prisms is adjustable. Thereby, a plurality of different rotation patterns can be generated. In particular, a corresponding control by means of an electronic computing device or by means of one or more control device(s) then occurs. Depending on the desired different rotation patterns, the respective distances can then be adjusted.

Further, it can be provided that the respective Risley prisms of the Risley prism pair are formed to be rotated with different rotational speeds. The control with different rotational speeds can be effected via the control device(s) of the beam deflection device. Thereby, it is allowed that highly complex rotation patterns can be generated in or on the material. Thus, different rotation patterns can be generated for different purposes of employment of the laser device and the laser device is flexibly employable.

In a preferred embodiment of the beam deflection device, the beam deflection device comprises at least one dual MEMS mirror pair as well as a Risley prism pair, wherein the Risley prism pair in particular has a fixed distance to each other, is oriented at 180 degrees to each other and is arranged fixed to each other such that they are operated with the same rotational speed. In the preferred embodiment, the beam deflection device is provided for a laser device formed as an eye surgical laser. Then, the laser device is in particular formed as a rotation scanner.

It is further advantageous if the beam deflection device comprises a control device, which is formed for controlling the reflecting or dispersive beam offset element and the rotating, dispersive optical element. In particular, the control device can be formed to control both the reflecting or dispersive beam offset element and the rotating, dispersive optical element coordinated with each other. In particular, the beam offset element and the optical element are controlled such that the rotation pattern can be generated in or on the material.

The beam deflection device can also comprise a plurality of control devices for controlling the reflecting or dispersive beam offset element and the rotating, dispersive optical element, wherein plurality presently means more than one control device. The control device of the beam deflection device can also function as a control device of the laser device and thus generate further control signals for the laser device.

A second aspect of the invention relates to a laser device with at least one laser generating device and with at least one beam deflection device according to the first aspect. Preferably, the laser device is formed as an ophthalmological treatment device. In a further advantageous form of configuration, the control device of the laser device comprises at least one storage device for at least temporary storage of at least one control dataset, wherein the dataset or datasets include(s) control data for positioning and/or for focusing a laser beam in or on a material, for example a cornea of a patient. Alternatively, the laser device can also include more than one control device. Thus, the laser device is preferably formed as a rotation scanner.

Further, it is in particular provided that the laser generating device is formed to emit laser pulses in a wavelength range between 100 nanometers and 15 micrometers, in particular between 700 nanometers and 1200 nanometers, at a respective pulse duration between one femtosecond and one nanosecond, in particular between 10 femtoseconds and 10 picoseconds, and a repetition frequency of greater than 1 kilohertz, in particular between 100 kilohertz and 500 kilohertz. Preferably, it can be provided that the laser device is thus formed for treating a cornea of a patient. Thus, in particular, both ablation techniques can be applied and lenticules can be generated by photodisruption.

A third aspect of the invention relates to a method for generating a laser pattern in or on a material by means of a laser beam and by means of a beam deflection device for a laser device, in which the laser beam of a laser generating device of the laser device is spatially offset in relation to an optical axis of the laser generating device by means of at least one reflecting or dispersive beam offset element, and in which a rotation pattern is generated as the laser pattern from the previously offset laser beam by means of a rotating, dispersive optical element.

A fourth aspect of the invention relates to a computer program including instructions, which cause the beam deflection device according to the first inventive aspect to perform the method aspects according to the third inventive aspect. A fifth aspect of the invention relates to a computer-readable medium, on which the computer program according to the fourth inventive aspect is stored.

Further features and the advantages thereof can be taken from the descriptions of the first, the second and the third inventive aspect, wherein advantageous configurations of each inventive aspect are to be regarded as advantageous configurations of the respectively other inventive aspect.

Further features are apparent from the claims, the figures and the description of FIGURES. The features and feature combinations mentioned above in the description as well as the features and feature combinations mentioned below in the description of FIGURES and/or shown in the figures are usable not only in the respectively specified combination, but also in other combinations without departing from the scope of the invention. Thus, implementations are also to be considered as encompassed and disclosed by the invention, which are not explicitly shown in the figures and explained, but arise from and can be generated by separated feature combinations from the explained implementations. Implementations and feature combinations are also to be considered as disclosed, which thus do not comprise all of the features of an originally formulated independent claim. Moreover, implementations and feature combinations are to be considered as disclosed, in particular by the implementations set out above, which extend beyond or deviate from the feature combinations set out in the relations of the claims.

FIG. 1 shows a schematic view of an embodiment of a laser device with an embodiment of a beam deflection device.

In FIG. 1, identical or functionally identical elements are provided with the same reference characters.

FIG. 1 shows an embodiment of a laser device 10 in a schematic side view. The laser device 10 comprises at least one laser generating device 12 as well as a beam deflection device 14. Preferably, it can be provided that the laser device 10 is formed as an ophthalmological treatment device. Thereby, it is in particular allowed that a cornea of a patient can for example be treated.

Further, it is in particular provided that the laser device 10 comprises a control device 16, wherein the control device 16 comprises at least one storage device 18 for at least temporary storage of at least one control dataset, wherein the control dataset or datasets include(s) control data for positioning and/or focusing a laser beam 20. The laser generating device 12 is formed to emit laser pulses in a wavelength range between 100 nanometers and 15 micrometers, in particular between 700 nanometers and 1200 nanometers, at a respective pulse duration between one femtosecond and one nanosecond, in particular between 10 femtoseconds and 10 picoseconds, and a repetition frequency of greater than 1 kilohertz, in particular between 100 kilohertz and 500 kilohertz.

Further, the control device 16 in particular comprises a computer program as well as a computer-readable medium, wherein the computer program includes instructions, which cause the laser device 10 to perform a method according to the invention for generating a laser pattern 22 by means of the laser beam 20 and by means of the beam deflection device 14, in which the laser beam 20 is spatially offset to an optical axis 40 of the laser generating device 12 by means of at least one reflecting or dispersive beam offset element 24, and in which a rotation pattern 28 is generated as the laser pattern 22 from the previously offset laser beam 20 by means of a rotating, dispersive optical element 26.

Thus, for generating the laser pattern 22 in or on a material 38, for example a cornea of a patient, the beam deflection device 14 according to the invention comprises at least the reflecting or dispersive beam offset element 24 for spatially offsetting the laser beam 20, as well as the rotating, dispersive optical element 26, which is formed for generating the rotation pattern 28.

FIG. 1 in particular shows that the reflecting beam offset element 24 comprises at least one micro-optical electromechanical mirror element 30, 32, in particular presently two micro-optical electromechanical mirror elements 30, 32. In other words, a first micro-optical electromechanical (MEMS) mirror element 30 and a second micro-optical electromechanical mirror element 32 are presently shown. Thus, the reflecting beam offset element 24 is provided as a dual MEMS mirror. Alternatively, the reflecting beam offset element 24 can comprise at least one galvano mirror or comprise at least one prism or at least one Risley prism 34, 36 or at least one Dove prism as the dispersively configured beam offset element 24.

The rotating, dispersive optical element 26 is in particular formed as a Risley prism pair 34, 36. In the present embodiment, respective Risley prisms 34, 36 of the Risley prism pair 34, 36 are arranged rigidly fixed to each other and in particular have a relative angle Φ of substantially 180 degrees to each other. Further, it is in particular provided that the respective Risley prisms 34, 36 have a fixed distance d to each other in an optical path of the laser device 10 and along the optical axis 40, respectively. In the present embodiment, the respective Risley prisms 34, 36 are further formed such that they are rotated with an identical rotational speed Θ.

Alternatively hereto, it can be provided that the respective Risley prisms 34, 36 have an adjustable distance d to each other in the optical path of the laser device 10. Herein, it can further be provided that the respective Risley prisms 34, 36 are additionally or instead rotated with different rotational speeds Θ.

By the combination of the beam deflection element 24 and the rotating, dispersive optical element 26, the laser beam 20 spatially offset by the beam deflection element 24 is transferred into the rotation pattern 28. In FIG. 1, the beam offset is identified by r and the transfer into the rotation pattern 28 is indicated by R. Further, it can be provided that the material has a fixed distance D to the optical element 26, whereby a simply configured laser device 10 can be provided. Alternatively, the distance D can also be variably adjusted such that complex laser patterns 22 can also be generated. By means of the control device 16, a control respectively coordinated with each other and in particular a position alteration of the beam deflection element 24 and the optical element 26 respectively coordinated with each other can be performed.

In the example shown in FIG. 1, thus, in particular from different concepts, such as for example the dual MEMS mirror pair, which is biaxially formed, and the rigidly coupled Risley prism pair 34, 36, the respective advantages can be utilized and the disadvantages thereof can be compensated for. The dual MEMS mirror pair is in particular formed for a substantially parallel beam offset without angle alteration to the optical axis 40, wherein a spiral or other non-circular scan patterns can be realized by means of a synchronous position decompensation of the beam deflection element 24. Thereby, a decentered treatment can for example be performed on a cornea, for example, the offset laser beam 20 of the MEMS mirrors impinges on a certain point of impingement on the Risley prism pair 34, 36. By the relative angle of 180° of the two Risley prisms 34, 36, the influence on the beam profile becomes negligible, wherein vibrations are also negligible since a concentric construction and prisms oriented rigidly to each other prevent it. Thereby, a simplified system can be realized since different rotational speeds Θ are not required.

Thus, FIG. 1 shows that a rotation scanner can be provided in particular for an ophthalmological treatment device, which uses the dual MEMS mirrors for the parallel beam offset without angle alteration, such that a spiral or other non-circular scan patterns can be realized by means of synchronous position decompensation of the MEMS mirrors. The generation of the rotation pattern 28 is then realized by means of the offset laser beam 20 by the rotating Risley prism pair 34, 36.

What is claimed is:

1. A beam deflection device for a laser device for generating a laser pattern on or in a material by means of a laser beam of the laser device, comprising:
   at least one reflecting beam offset element or at least one dispersive beam offset element, which is formed for spatially offsetting the laser beam in relation to an optical axis of a laser generating device of the laser device; and
   a rotating, dispersive optical element, which is formed for generating a rotation pattern as the laser pattern from a previously offset laser beam.

2. The beam deflection device according to claim 1, wherein the at least one reflecting beam offset element comprises at least one micro-optical electromechanical mirror element.

3. The beam deflection device according to claim 1, wherein the at least one reflecting beam offset element comprises at least two micro-optical electromechanical mirror elements.

4. The beam deflection device according to claim 1, wherein the at least one reflecting beam offset element comprises at least one galvanometer mirror or the at least one dispersive beam offset element comprises at least one prism or at least one Risley prism or at least one Dove prism.

5. The beam deflection device according to claim 1, wherein the rotating, dispersive optical element is formed as a Risley prism pair.

6. The beam deflection device according to claim 5, wherein respective Risley prisms of the Risley prism pair are arranged rigidly fixed to each other.

7. The beam deflection device according to claim 6, wherein the Risley prisms of the Risley prism pair are fixed at a relative angle of substantially 180° to each other.

8. The beam deflection device according to claim 5, wherein respective Risley prisms of the Risley prism pair have a fixed distance to each other along the optical axis of the laser generating device.

9. The beam deflection device according to claim 5, wherein respective Risley prisms of the Risley prism pair have a variably adjustable distance to each other along the optical axis of the laser generating device.

10. The beam deflection device according to claim 5, wherein respective Risley prisms of the Risley prism pair are formed to be rotated with rotational speeds different from each other.

11. The beam deflection device according to claim 1, wherein the beam deflection device comprises a control device, which is formed for controlling the reflecting beam offset element or the dispersive beam offset element and the rotating, dispersive optical element.

12. A laser device comprising:
    at least one laser generating device; and
    at least one beam deflection device according to claim 1.

13. The laser device according to claim 12, wherein the laser device is configured to perform an ophthalmological treatment.

14. The laser device according to claim 13, wherein at least one control device of the laser device comprises at least one storage device for at least temporary storage of at least one control dataset, wherein the at least one control dataset includes control data for positioning and/or for focusing a laser beam in a cornea.

15. The laser device according to claim 12, wherein the laser generating device is formed to emit laser pulses in a wavelength range between 100 nm and 15 μm, or between 700 nm and 1200 nm, at a respective pulse duration between 1 fs and 1 ns, or between 10 fs and 10 ps, and a repetition frequency of greater than 1 kHz, or between 100 kHz and 50 MHz.

16. A method for generating a laser pattern in or on a material by means of a laser beam and by means of a beam deflection device for a laser device, comprising:
    spatially offsetting the laser beam of a laser generating device of the laser device along an optical axis of the laser generating device by means of at least one reflecting beam offset element or dispersive beam offset element of the beam deflection device; and
    generating a rotation pattern as the laser pattern from a previously offset laser beam by means of a rotating, dispersive optical element of the beam deflection device.

17. A non-transitory computer-readable medium, on which a computer program is stored, the computer program, including instructions, which cause the laser device having the laser generating device and the beam deflection device to perform the method according to claim 16.

* * * * *